United States Patent [19]

Antonov et al.

[11] 4,086,366

[45] Apr. 25, 1978

[54] PRODUCTION OF VODKA

[76] Inventors: Sergei Fedorovich Antonov, ulitsa A. Tolstogo 18, kv. 34, Moscow; Pavel Firsovich Krasheninin, Krasnoarmeisky bulvar 14, kv. 5, Uglich Yaroslavskoi oblasti; Vyacheslav Mikhailovich Bogdanov, ulitsa Rustaveli 19, kv. 130, Moscow; Andrei Georgievich Khramtsov, ulitsa Lenina 399, kv. 14, Stavropol; Gennady Efimovich Eremin, ulitsa Instrumentalnaya 10, kv. 32, Uglich Yaroslavskoi oblasti, all of U.S.S.R.

[21] Appl. No.: 688,031

[22] Filed: May 19, 1976

[51] Int. Cl.$^2$ .............................................. C12C 11/08
[52] U.S. Cl. .................................... 426/14; 426/41; 426/60; 426/422; 426/494
[58] Field of Search .................... 426/11, 14, 41, 592, 426/422, 494, 583, 60; 195/37

[56] References Cited

PUBLICATIONS

Webb, et al., Byproducts from Milk, 2nd ed. The Avi Pub. Co., Inc. Westport, Conn. 1970 (pp. 34–37, 58 & 59).

Herstein et al., Chemistry and Technology of Wines and Liquors, D. Van Nostrand Co., Inc., N.Y., 1948, (pp. 176 & 177).

Amerine et al., The Technology of Wine Making, 3rd ed. The Avi Pub. Co., Inc., Westport, Conn. 1972, (pp. 309–318).

*Primary Examiner*—David M. Naff
*Attorney, Agent, or Firm*—Steinberg & Blake

[57] ABSTRACT

Vodka is produced by a process involving fermenting pre-pasteurized and cooled whey with Candida or Torulopsis yeast to form a mash containing ethanol and products of proteolysis, recovering the ethanol and products of proteolysis from the mash, rectifying the ethanol and purifying it from the products of proteolysis and diluting the resultant purified ethanol with deproteinized whey. This process makes it possible to make a high quality vodka and replace scarce grain, potato and beet raw materials currently used to produce vodka.

7 Claims, No Drawings

PRODUCTION OF VODKA

The present invention relates to the food industry and, more specifically, to a process for the production of vodka; it may be used mainly in the milk-production industry.

Currently used is a process for the production of vodka from a carbohydrate-containing vegetable raw materials such as grain, potato, beet.

This known process comprises fermentation of sugar contained in these raw materials to ethanol by means of baker's yeast. Thereafter, from ethanol is recovered the resulting mash, rectified and mixed with water to a required alcohol concentration, i.e. to 30–45% by weight.

The principal disadvantage of this prior art process resides in the use, as the starting materials for the production of vodka, of valuable food products which are of vital importance for human nutrition.

At the present time, due to population growth and the constantly aggravating need for foodstuff products, the problem of replacing traditional starting raw materials for the production of vodka with other less scarce materials is of primary importance.

It is an object of the present invention to provide an economically efficient process for the production of high-quality vodka.

This and other objects of the present invention are accomplished in the process of the production of vodka by fermentation of the starting carbohydrate-containing raw materials, recovery of ethanol from the resulting mash, rectification thereof and dilution to a content of alcohol in the final product of from 30 to 45% by weight, by utilizing in accordance with the present invention as the starting carbohydrate-containing material use of whey pre-pasteurized and cooled to a temperature of from 28° to 30° C which is fermented by yeast of the Candida or Torulopsis species. After rectification, ethanol is purified from the products of proteolysis, whereafter dilution of ethanol is effected by means of whey previously purified from proteins to a content thereof of up to 0.05 wt.%.

The use of whey in the production of vodka makes it possible to replace scarce food raw materials; introduction of operations of additional purification of ethanol from the products of proteolysis and dilution thereof with whey purified from proteins ensures the production of vodka which is not inferior to that produced from grain.

It is advisable to employ, as yeast for fermentation, strains "SK" or "IIA" of yeast *Torulopsis sphaerica* or strain *Candida pseudotropicalis var. lactosa* 85.

Said strains are kept in the collection of the Vsesojuyzny Nauchno-Issledovatelsky Institut Maslodelnoj i Syrodelnoj Promyschlennosti (USSR Research Institute of Butter and Cheese Industry).

The strain of yeast *Candida pseudotropicalis var. lactosa* 85 is recovered from sour milk matzoon, followed by inoculation thereof onto wort agar in Petri dishes and reinoculation onto askew wort agar into test-tubes; the isolated strain has the following morphological features and physiological properties: cell size of two-days culture on wort agar — 3–5μ dominating shape of cells — oval; propagation by budding on the Gorodkova medium of the composition:

distilled water: 1,000 ml
agar: 10 g
peptone: 10 g
meat extract: 10 g
common salt: 5 g
grape sugar: 2.5 g it does not form spores; neither does it dilute gelatine;

when inoculated onto wort agar in Petri dishes, after 5 days at a temperature of 25° C, it forms whitish colonies with an even edge and diameter of 1–2 cm;

when grown in cheesy whey it forms a uniform sludge;

attitude to carbohydrates — fermentive in respect of glucose, lactoglucose, lactose, saccharose; yield of ethanol 2.0% by weight.

The yeast strain *Torulopsis sphaerica* "SK" is recovered from kefir yeast, followed by inoculation thereof onto wort agar in Petri dishes and reinoculation onto askew wort agar in test-tubes; the isolated strain has the following morphological features and physiological properties:

cell size of two-days culture on wort agar, 3–5μ;
dominating cell shape — round;
propagation — by budding;
no spores formed on the Gorodkova medium;
gelatine is not diluted therewith;

when inoculated in Petri dishes with wort agar, it forms whitish colonies with a diameter of 1–2 cm after 5 days at a temperature of 25° C;

when grown in cheesy whey, it forms a uniform sludge, a thin film;

attitude to carbohydrates: it is fermentive in respect of glucose, lactoglucose, lactose, saccharose, raffinose, xylose;

the yield of ethanol is 2.3% by weight.

The yeast strain, *Torulopsis sphaerica* "IIA" is recovered from kumyss with subsequent inoculation thereof onto wort agar in Petri dishes and reinoculation onto askew wort agar in test-tubes; the isolated strain has the following morphological characteristics and physiological properties;

two-days' culture cell size — 2–6μ;
dominating cell shape — rounded;
propagation — by budding;
no spores formed on the Gorodkova medium;
gelatine is not diluted therewith;

when inoculated in Petri dishes onto wort agar, it forms, after 5 days at the temperature of 25° C, cream-coloured colonies;

diameter of the colonies — 1–2 cm;

when grown in cheesy whey, it forms a uniform sludge, a thin film;

attitude to carbohydrates: fermentive in respect of glucose, lactoglucose, lactose, saccharose;

the yield of ethanol is 2.1% of weight.

It is possible to use, for the fermentation purposes, a mixture of at least two of the two above-described strains.

To ensure most complete fermentation of whey carbohydrates to ethanol, it is advisable that the yeast be used in an amount within the range of from 15 to 20% by weight and the fermentation stage be conducted for a period of from 48 to 72 hours.

It is most advantageous to purify ethanol from the products of proteolysis by adding skim milk thereto in an amount ranging from 5 to 10% by weight; maintaining the resulting mixture at a temperature within the range of from 20° to 30° for a period of 20 to 60 minutes and removing proteins coagulated thereon.

Incorporation of the above-mentioned amount of skim milk ensures the most complete removal of the products of deep proteolysis as well as fusel oils and aldehydes and imparts specific organoleptic characteristics to the final product.

To ensure an increased yield of ethanol, it is advisable to use, as the starting material, whey with an acidity of 16° to 18° T.

The process for the production of vodka according to the present invention is preferably embodied in the following manner.

Whey is pasteurized, separated from proteins by any conventional method and cooled to a temperature of from 28° to 30° C.

Use can be made of any whey, either cheesy or curd whey. However, as it has been shown by experimental investigations, it is most advantageous to employ fresh cheesy whey with an acidity of 18° T at most. The use of whey with a higher acidity results in the yield of ethanol being reduced, since it contained a lesser amount of lactose due to its partial fermentation by means of lactic bacteria to lactic acid.

A cooled whey is incorporated, for the fermentation purposes, with milk yeast leaven, containing yeast of the Candida or Torulopsis species in an amount of from 15 to 20% by weight of the whey.

Said amount of leaven incorporated into whey appears to be optimal from consideration of ensuring a required completeness and rate of fermentation with most economically efficient consumption rate of leaven. The latter can be incorporated in amounts exceeding or inferior to that indicated hereinbefore. This will result in acceleration of lactose fermentation or retardation thereof; the former is achieved at the account of unreasonably high consumption rate of yeast leaven.

The milk yeast leaven employed for fermentation of lactose can be prepared by means of one of the yeast strains *Torulopsis sphaerica* "SK" or "IIA", *Candida pseudotropicalis varlactose* 85 or a mixture thereof in any possible combination.

The milk yeast leaven is prepared in the following manner.

Preliminary prepared is a "mother" culture of the selected yeast species. It is prepared in much the same manner for both an individual strain and a mixture of strains. The "mother" culture is prepared on the basis of a sterile whey by way of growing therein an individual yeast strain or a mixture of strains for 24 hours at the temperature of 28°–30° C. Thereafter, the resulting "mother" culture (about 1 billion of cells) is introduced into sterile whey in an amount of from 15 to 20% by weight and this mixture is maintained for 24 hours at a temperature of from 28° to 30° C. The resulting working milk-yeast leaven containing about 500 mln. of cells per 1 ml is introduced into whey for fermentation.

A mixture of whey and yeast leaven is maintained at a temperature of from 28° to 30° C for a period of from 48 to 72 hours. This temperature is optimal for growth of cells of the above-mentioned yeast strains. The above-indicated duration of this maturation period ensures practically complete fermentation of lactose to ethanol.

Said residence time within the above-indicated limits depends on the amount of yeast incorporated and the strain type.

As a result, a mash is obtained which is then distilled (subjected to fractionation). The thus-recovered ethanol is rectified and then subjected to additional purification to remove the products of proteolysis.

This operation can be performed by any of conventional methods such as gel-filtration, reverse osmosis, electrodialysis. However, from the considerations of processability, economic efficiency and simplicity of process equipment it is advisable to employ, at the time being, skim milk for the removal of alcohol from non-alcoholic components.

To this end, skim milk is introduced into ethanol in an amount of from 5 to 10% by weight at a temperature within the range of from 20° to 25° C for a period of from 20 to 60 minutes and the coagulated proteins are separated. Upon introduction of skim milk into ethanol, denaturation and coagulation of the proteins contained therein occurs. During the coagulation, protein globules "capture" and adsorb the products of proteolysis present in ethanol as well as fusel oils, aldehydes and other non-alcoholic components. Thereby a thorough purification of ethanol is achieved.

To obtain the final product, the purified ethanol is mixed with whey pre-exempted from porteinaceous substances. The content of the latter substances in whey employed for dilution of ethanol should not exceed 0.05% by weight.

The intermixed components, i.e. ethanol and whey, are employed in a the ratio ensuring the content of alcohol in the final production of from 30 to 45% by weight.

The final product is thus prepared which has the following chemical composition:
alcohol: 45%
lactose: 2.5%
lactic acid: 0.1%
fat: 0.03%
free aminoacids: 0.02%
vitamins: 1.3 mg/%
mineral salts: 0.35%
including
macroelements: 0.23%
microelements: 0.0001%
aldehydes, at most: 1 mg/l
fusel oils, at most: 1.5 mg/l
ethers, at most: 13 mg/l.

Vodka, prepared from whey according to the process of the present invention has a clearly pronounced "soft" taste, specific pleasant smell and lemon colour with a greenish tint.

The process according to the present invention makes it possible to obtain 20–25 l of food-grade ethanol with up to 93% strength from 1 ton of whey. In addition, as a by-product it is also possible to obtain from 1 ton of the starting material about 30 kg of whey alimentary protein in the form of nutritive albumin curds and about 40 kg of dry feed-grade yeast contributing to an increased productivity of animal husbandry.

Production of one ton of ethanol from whey makes it possible to save up to 12 tons of potato and up to 3.0–35. tons of grain.

For better understanding of the present invention, some specific examples illustrating the process for the production of vodka are given hereinbelow.

EXAMPLE 1

1,000 kg of whey with the acidity of 16° T are heated to a temperature of 95° C, 2 l of concentrated hydrochloric acid are added thereto and the mixture is maintained at the above-indicated temperature for 20 minutes, then cooled to 60° C and purified from proteins in a self-emptying separator.

960 kg of the purified whey are cooled to a temperature of 28° to 30° C and 190 kg of a working milk-yeast leaven prepared by growing, for 24 hours at a temperature of 28°–30° C, the yeast strain *Torulopsis sphaerica* "*IIA*" in a sterile whey are added.

This mixture is maintained at a temperature of from 28° to 30° C for 48 hours. The resulting mash contains 3% by weight of alcohol. Distillation of the mash results in 26 l of crude ethanol. The stillage remaining after isolation of alcohol is dried and used as animal feed.

The crude alcohol is subjected to rectification. Then, in order to purify ethanol from the products of proteolysis, 1.5 l of skim milk are added. The resulting mixture is maintained at a temperature of 20° C for 50 minutes and the coagulated proteins are separated by filtration to give 23 l of food-grade ethanol with the alcohol content of 91% by weight. Then, this alcohol is diluted with 30 l of whey purified from proteinaceous substances to the content thereof of 0.05% by weight. As a result, 53 l of vodka with the alcohol content of 40% by weight are obtained.

EXAMPLE 2

Into 1,000 kg of whey with the acidity of 18° T and treated in a manner similar to that described in the foregoing Example 1 150 kg of the working milk-yeast leaven are introduced which is prepared by growing the yeast strain *Torulopsis sphaerica* "SK" for 24 hours at a temperature of 28°–30° C in a sterile whey.

Said mixture is maintained at a temperature of 28° to 30° C for 72 hours. From the resulting mash 27 l of crude ethanol are distilled-off. Further operations of the process are performed in a manner similar to that of Example 1 to give 55 l of vodka with the alcohol content of 40%.

EXAMPLE 3

Into 1,000 kg of whey with the acidity of 18° T treated as described in Example 1, 150 kg of milk-yeast whey prepared by growing the yeast strain *Candida pseudotropicalis var. lactosa* 85 for 24 hours at a temperature of 28° to 30° C in a sterile whey are introduced. The resulting mixture is maintained at a temperature of 28° to 30° C for 72 hours. After distillation of the thus-prepared mash 24.5 l of crude ethanol are obtained. Further treatment is performed as described in Example 1 hereinbefore to give 50 l of vodka with the alcohol content of 40% by weight.

EXAMPLE 4

Into 1,000 kg of whey with the acidity of 18° T treated in a manner similar to that described in Example 1, there are introduced 190 kg of milk-yeast leaven prepared by growing a mixture of yeast strains Torulopsis sphaerica "IIA" and "SK" and yeast strain *Candida pseudotropicalis var. lactosa* 85 (50, 90 and 50 kg respectively) in a sterile whey at a temperature of 28° to 30° C for 24 hours. Fermentation is conducted for 48 hours at a temperature of from 28° to 30° C. From the thus-prepared mash 27 l of crude ethanol are distilled-off.

Further treatment is effected in a manner similar to that described in Example 1 hereinbefore to give 55 l of vodka with the alcohol content of 40 % by weight.

EXAMPLE 5

1,000 kg of curds whey with the acidity of 80° T are heated to a temperature of 95° C and sodium hydroxide is added thereto to reduce acidity down to 35° T. Further stages of the process are performed in a manner similar to that described in Example 1 hereinbefore.

Distillation results in 18 l of ethanol with the alcohol content of 92% of weight.

After dilution thereof with whey 38 l of vodka are obtained with the alcohol content of 40% by weight.

What is claimed is:

1. A process for the production of vodka from whey which comprises fermenting for a period of 48-72 hours pasteurized whey cooled to a temperature of 28° to 30° C with 15–20% by weight of at least one of the yeasts *Candida psuedotropicalis var. lactosa* 85, *Torulopsis sphaerica* "SK" and *Torulopsis sphaerica* "IIA", thereby forming a mash containing ethanol and products of proteolysis, recovering said ethanol and products of proteolysis from the resulting mash, rectifying the ethanol and purifying it from said products of proteolysis, diluting the purified ethanol to an ethanol content of 30 to 45% by weight by mixing the purified ethanol with deproteinized whey containing a maximum of 0.05% protein by weight.

2. A process as claimed in claim 1, wherein as the yeast for fermentation use is made of the yeast strain *Candida pseudotropicalis var. lactosa* 85.

3. A process as claimed in claim 1, wherein as the yeast for fermentation use is made of the yeast strain *Torulopsis sphaerica* "SK".

4. A process as claimed in claim 1, wherein as the yeast for fermentation use is made of the yeast strain *Torulopsis sphaerica* "IIA".

5. A process as claimed in claim 1, wherein as the yeast for fermentation use is made of at least two strains selected from the group consisting of the yeast strains *Torulopsis sphaerica* "SK" and "IIA" and *Candida pseudotropicalis var. lactosa* 85.

6. A process as claimed in claim 1, wherein purification of ethanol from the products of proteolysis is effected by adding, to ethanol, skim milk in an amount of from 5 to 10% by weight, maintaining the resulting mixture at a temperature of from 20° to 30° C for a period of from 20 to 60 minutes and eliminating the proteins coagulated therewith.

7. A process as claimed in claim 1, wherein the whey has an acidity of 16° to 18° T.

* * * * *